(12) United States Patent
Shimada et al.

(10) Patent No.: US 6,488,857 B1
(45) Date of Patent: Dec. 3, 2002

(54) METHOD OF SEPARATING HEMOGLOBIN $A_2$

(75) Inventors: Kazuhiko Shimada, Tokuyama (JP); Yuji Setoguchi, Shinnanyo (JP); Kazuyuki Oishi, Tokuyama (JP); Toshiki Kawabe, Shiga (JP)

(73) Assignee: Sekisui Chemical Co., Ltd., Osaka (JP)

( * ) Notice: Subject to any disclaimer, the term of this patent is extended or adjusted under 35 U.S.C. 154(b) by 35 days.

(21) Appl. No.: 09/806,518
(22) PCT Filed: Sep. 22, 2000
(86) PCT No.: PCT/JP00/06488
§ 371 (c)(1),
(2), (4) Date: Apr. 18, 2001
(87) PCT Pub. No.: WO01/22077
PCT Pub. Date: Mar. 29, 2001

(30) Foreign Application Priority Data

Sep. 24, 1999 (JP) .............................. 11-271036
Jul. 28, 2000 (JP) ........................ 2000-229328

(51) Int. Cl.⁷ ............................................. B01D 15/08
(52) U.S. Cl. .................... 210/656; 210/635; 210/198.2; 530/385; 530/416; 436/66
(58) Field of Search ................. 210/635, 656, 210/198.2, 659; 530/385, 413, 416, 417; 436/66

(56) References Cited

U.S. PATENT DOCUMENTS

| 4,810,391 A | 3/1989 | Bruegger ..................... 210/656 |
| 5,821,351 A | 10/1998 | Kumar et al. .............. 536/23.4 |
| 5,952,482 A | 9/1999 | Kumar et al. .............. 536/23.4 |

FOREIGN PATENT DOCUMENTS

| JP | 10-227780 | * 8/1998 | ................. 210/656 |
| JP | 10-300741 | * 11/1998 | ................. 210/656 |
| JP | WO 00/08460 | * 2/2000 | ................. 210/656 |
| JP | 2000-111538 | * 4/2000 | ................. 210/656 |

* cited by examiner

Primary Examiner—Ernest G. Therkorn
(74) Attorney, Agent, or Firm—Townsend & Banta (57) ABSTRACT

A method for separating hemoglobin $A_2$ from a hemoglobin mixture according to a cation exchange liquid chromatography characterized that at least two types of eluents are used including an eluent (hereinafter referred to as "eluent A") for elution of faster hemoglobins than hemoglobin $A_0$ and an eluent (hereinafter referred to as "eluent B") for elution of hemoglobin $A_0$ and slower hemoglobins than hemoglobin $A_0$, and that the eluent A has a pH of 4.0–6.0 and the eluent B is maintained at a pH of at least 0.5 higher than that of the eluent A.

13 Claims, 7 Drawing Sheets

METHOD OF SEPARATING HEMOGLOBIN $A_2$

REFERENCE TO RELATED APPLICATIONS

This application is a 371 of PCT/JP00/06488 filed Sep. 22, 2000.

TECHNICAL FIELD

The present invention relates to a method for separating hemoglobin $A_2$ by cation exchange liquid chromatography.

BACKGROUND ART

Hemoglobin $A_2$ is composed of $\alpha$ and $\delta$ chains, and is used, like hemoglobin F, as a diagnostic indicator of Mediterranean anemia (thalassemia). For testing of Mediterranean anemia, cation exchange liquid chromatography is generally employed to separate from a hemoglobin mixture and quantitate hemoglobin $A_2$ (hereinafter referred to as $HbA_2$).

Separation of a hemoglobin mixture, i.e., a hemolyzed sample, with the use of cation exchange liqud chromatography generally results in the appearance of peaks of hemoglobin $A_{1a}$ (hereinafter referred to as $HbA_{1a}$) and hemoglobin $A_{1b}$ (hereinafter referred to as $HbA_{1b}$), hemoglobin F (hereinafter referred to as HbF), labile hemoglobin $A_{1c}$, (hereinafter referred to as labile $HbA_{1c}$), stable hemoglobin $A_{1c}$ (hereinafter referred to as stable $HbA_{1c}$), hemoglobin $A_0$ (hereinafter referred to as $HbA_0$) and the like. On this occasion, an extended time has been required to achieve complete separation of $HbA_0$ and $HbA_2$ from each other since they show the similar retention behaviors with respect to a cation exchange column and their peaks occur in close proximity to each other.

One method of separating $HbA_2$ from a hemoglobin (hereinafter referred to as Hb) mixture is disclosed, for example, in U.S. Pat. No. 4,810,391 which utilizes a weak cation exchange packing material and is characterized by the use of three types of buffering eluents having different phosphate concentrations and pH's. A first eluent is a phosphate buffer maintained at a concentration of 1–20 mm and at a pH of 6.5–6.9 for use in elution of $HbA_{1a}$ and $HbA_{1b}$. A second eluent is a phosphate buffer maintained at a concentration of 15–55 mM and at a pH of 6.4–6.8 for use in elution of $HbA_{1c}$ and $HbA_0$. A third eluent is a phosphate buffer maintained at a concentration of 60–100 mM and at a pH of 6.4–6.8 for use in elution of $HbA_2$.

EP-0315187 discloses a method for quantification of $HbA_2$ wherein $HbA_{1a}$ and $HbA_{1b}$ are eluted by a first eluent, $HbA_{1c}$ and $HbA_0$ by a second eluent and $HbA_2$ by a third eluent.

However, in the above-described methods, the eluents are distinguished from each other substantially by the salt concentration only. This extends a measurement time and prevents quick separation and measurement of a lot of specimen, which have been problems. Another problem arises when $HbA_2$ and $HbA_{1c}$ are concurrently separated and measured, i.e., precise measurement of $HbA_{1c}$ is disturbed significantly by the insufficient separation of $HbA_{1c}$ Also, the pH's of the eluents are lower than an isoelectric point of hemoglobin. This creates another problem, i.e., increases the tendency of Hb and other blood components to be adsorbed on packing material to thereby shorten a column service life.

In view of the above-described problems encountered in conventional methods of separating $HbA_2$ from a Hb mixture, an object of the present invention is to provide a method which enables quicker and more precise separation of $HbA_2$ than conventional methods.

DISCLOSURE OF THE INVENTION

A first invention of the present application is a method for separating hemoglobin $A_2$ from a hemoglobin mixture by cation exchange chromatography, characterized in that at least two types of eluents are used including an eluent (eluent A) for elution of faster hemoglobins than hemoglobin $A_0$ and an eluent (eluent B) for elution of hemoglobin $A_0$ and slower hemoglobins than hemoglobin $A_0$, and that the eluent A has a pH of 4.0–6.0 and the eluent B is maintained at a pH of at least 0.5 higher than that of the eluent A.

In a particular aspect of the first invention, the eluent B is maintained at a salt concentration lower than that of the eluent A.

In a more limited aspect of the first invention, an eluent (eluent D) is further used for elution of at least hemoglobin $A_2$. The eluent D is maintained at a pH of at least 0.5 lower than that of the eluent B.

In a more limited aspect of the first invention, a salt concentration of the eluent B is rendered lower than that of the eluent A and a salt concentration of the eluent D is rendered higher than that of the eluent B.

In a further particular aspect of the first invention, an eluent (eluent C) is further used having an elution power weaker than those of the eluents B and D. Those eluents are delivered in the sequence of B, C and D.

In a further particular aspect of the first invention, an eluent (eluent H) at a pH of 6.8–12 is delivered to follow the eluent B, or alternatively, to follow the eluent D when the eluents B and D are used in combination. The eluent H preferably contains a chaotropic ion.

A second invention of the present application is a method for separating hemoglobin $A_2$ from a hemoglobin mixture by cation exchange chromatography, characterized by the use of at least two types of eluents including an eluent (hereinafter referred to as "eluent E") which contains a chaotropic ion and also contains an inorganic acid, organic acid and/or any salt thereof having a buffer capacity at a pH of 4.0–6.8 and an eluent (hereinafter referred to as "eluent F") which contains an inorganic acid, organic acid and/or any salt thereof having a buffer capacity at a pH of 6.5–8.0.

In a particular aspect of the second invention, an eluent (hereinafter referred to as "eluent G") is further used having a lower pH and a higher salt concentration than the eluent F. The eluent G is delivered to follow the eluent F.

In a further aspect of the second invention, an eluent (eluent H) at a pH of 6.8–12 is delivered to follow the eluent F or G. Preferably, the eluent H contains a chaotropic ion.

In another particular aspect of the first or second invention, an azide ion is incorporated in at least one type of eluent and/or a hemolyzing solution.

In a further particular aspect of the first or second invention, a packing material is employed having at least one type of strong cation exchange group.

The first invention is now described.

In the first invention, "an eluent (referred to in this specification as "eluent A") used to elute faster hemoglobins than hemoglobin $A_0$" refers to the eluent used to elute Hb's that exhibit shorter retention time than $HbA_0$ while the hemoglobin mixture is subjected to separation by cation exchange liquid chromatography. General examples of Hb's to be eluted by the eluent A include $HbA_{1a}$, $HbA_{1b}$, HbF, labile $HbA_{1c}$, stable $HbA_{1c}$ and the like. It should be understood that not all of the above-listed Hb's but at least one type thereamong is needed to be eluted by the eluent A. The first invention, while its primary object is to separate $HbA_2$, also enables the separation and quantitation of stable $HbA_{1c}$ by performing elution of $HbA_{1a}$, $HbA_{1b}$, HbF, labile $HbA_{1c}$ and stable $HbA_{1c}$ with the aid of the eluent A.

The eluent A has a pH of 4.0–6.0, preferably of 4.5–5.8. If a pH of the eluent A is below 4.0, denaturation of hemoglobin may be caused to occur. If a pH of the eluent A exceeds 6.0, hemoglobins may be charged less positively to reduce its tendency to be retained by the cation exchange group, resulting in its reduced resolution. The eluent A is not necessarily a single type of eluent, and may be an eluent group A consisting of plural types of eluents having differing compositions and elution powers (in the case where the eluent A consists of n types of eluents, they are hereafter designated "eluent A1, eluent A2, . . . , eluent An"), so long as the eluent group A satisfies the above-specified conditions required for the eluent A. When desired to separate and quantitate stable $HbA_{1c}$, as well as $HbA_2$, within a shorter period of time, the eluent components A1, A2, A3 and the like may be delivered in a sequence of increasing elution power according to a linear gradient elution technique, a stepwise gradient elution technique or a combination thereof.

In the first invention, "an eluent (referred to in this specification as the "eluent B") used to elute hemoglobin $A_0$ and slower hemoglobins than hemoglobin $A_0$ " refers to the eluent used to elute $HbA_0$ and Hb's that exhibit the same retention time or longer retention time than $HbA_0$ while the hemoglobin mixture is subjected to separation by the cation exchange liquid chromatography. General examples of Hb's to be eluted by the eluent B include $HbA_0$, $HbA_2$, HbS, HbC and the like. It should be understood here that not all of the above-listed Hb's is needed to be eluted by the eluent B. The first invention may employ the eluents A and B only. In such a case, the eluent B is used to elute $HbA_0$, $HbA_2$ and the like. In the below-described case where an eluent D is used to elute $HbA_2$, the eluent B may be used to elute at least $HbA_0$. The eluent B may further elute stable $HbA_{1c}$ and labile $HbA_{1c}$, so long as the elution of at least $HbA_0$ is assured. Particularly when quantitation of HbF and $HbA_2$ only are effected, the elution of stable $HbA_{1c}$ by the eluent B permits quicker separation.

Characteristically, the pH of the eluent B is rendered higher than that of the eluent A by at least 0.5. This is because the pH of the eluent B, if rendered at least 0.5 higher than that of the eluent A, improves resolution of $HbA_0$. and $HbA_2$. More preferably, the pH of the eluent B is rendered at least 0.8 higher than that of the eluent A. The pH of the eluent B is preferably in the range of 6.0–8.0, i.e., in the neighborhood of a hemoglobin's isoelectric point (the Encyclopedia of Physics and Chemistry (4th ed., Iwanami Shoten, September 1987, edited by Ryogo Kubo et al.), at page 1178, describes the isoelectric point of hemoglobin as being pH 6.8–7.0). The eluent B is not necessarily a single type of eluent, and may be an eluent group B that consists of plural types of eluents having different compositions and elution powers (in the case where the eluent B consists of n types of eluents, they are hereafter designated "eluent B1, eluent B2, . . . , eluent Bn"), so long as the eluent group B satisfies the above-specified conditions required for the eluent B.

In the first invention, a salt concentration of the eluent B is preferably made lower than that of the eluent A. The salt concentration of an eluent, as used herein, means a total concentration of cations present in the eluent. The salt concentration of the eluent B, if rendered lower than that of the eluent A, further improves resolution of $HbA_0$ and $HbA_2$. The salt concentration of the eluent B is preferably made lower than that of the eluent A by at least 10 mM, more preferably by at least 30 mM.

Other than the eluents A and B, an additional eluent (referred to in the present specification as "eluent D") may preferably be used to elute at least hemoglobin $A_2$. The use of this eluent D further improves the resolution between $HbA_2$ and $HbA_0$ and also between $HbA_2$ and slower hemoglobins than $HbA_2$. This eluent D suffices if effective to elute at least $HbA_2$. Accordingly, in the case where the eluent D is effective to elute $HbA_2$ only, HbS, HbC and the like may be eluted either by the eluent D or another eluent, for example, by an eluent H as will be described below.

Characteristically, the pH of the eluent D is rendered lower than that of the eluent B by at least 0.5. The pH of the eluent D, if rendered at least 0.5 lower than that of the eluent B, further improves the resolution between $HbA_2$ and $HbA_0$, and also between $HbA_2$ and slower hemoglobins than $HbA_2$. More preferably, the pH of the eluent D is rendered lower than that of the eluent B by at least 0.8. The eluent D is not necessarily a single type of eluent, and may be an eluent group D which consists of plural types of eluents having differing compositions and elution powers (in the case where the eluent D consists of n types of eluents, they are hereafter designated "eluent D1, eluent D2, . . . , eluent Dn"), so long as the eluent group D satisfies the above-specified conditions required for the eluent D. The use of such an eluent group D not only permits precise separation of $HbA_2$ within a short period of time, but also enables separation and quantitation of HbS, HbC and the like.

In the case where the eluent D is used, it is preferred that the eluent B is kept at a salt concentration lower than that of the eluent A and that the eluent D is kept at a salt concentration higher than that of the eluent B. Preferably, the eluent B is maintained at a salt concentration at least 10 mM lower than that of the eluent A while the eluent D is maintained at a salt concentration at least 10 mM higher than that of the eluent B. More preferably, the eluent B is maintained at a salt concentration at least 30 mM lower than that of the eluent A while the eluent D is maintained at a salt concentration at least 30 mM higher than that of the eluent B.

In the first invention, besides the eluents A, B and C, an additional eluent (referred to in this specification as "eluent C") may further be used having a weaker elution power than the eluents B and D. In this case, those eluents can be delivered in the order of B, C and D. The use of such an eluent C retards elution of $HbA_2$ so that the more precise separation of $HbA_2$ can be achieved.

The eluent C may be maintained at any pH, so long as it has a weaker elution power than the eluents B and D. The eluent having a weak elution power, as used herein, refers to the eluent effective to retard elution of Hb's when the hemoglobin mixture is subjected to separation by cation exchange liquid chromatography. An elution power of an eluent can be weakened by various techniques, including reduction of a pH or salt concentration of the eluent. In the present case, the eluent C is rendered lower than the eluents B and D, in terms of either or both of a pH and a salt concentraion.

In the first invention, the eluents are delivered in the order of A and B, or in the order of A, B and D if D is also used, or in the order of A, B, C and D if C is also used. In general, the elution power is controlled to increase in the order of A, B and D.

The above-described eluents A–D (hereinafter referred to as "eluent", collectively, in the description of the first invention), for use in the first invention, comprise a buffer. The buffer may be used in the form of containing suitable additives which will be described later. Examples of buffer agents contained in the buffer include inorganic acids, organic acids and salts thereof which are illustrated below.

Examples of inorganic acids include phosphoric acid, boric acid, carbonic acid and the like.

Examples of organic acids include carboxylic acids, dicarboxylic acids, carboxylic acid derivatives, hydroxycarboxylic acids, amino acids, amines, imidazoles, pyridine, cacodylic acid, tris(hydroxymethyl)aminomethane, glycylglycine, pyrophosphoric acid and the like.

Examples of carboxylic acids include acetic acid, propionic acid and the like.

Examples of dicarboxylic acids include malonic acid, succinic acid, glutaric acid, adipic acid, maleic acid, fumaric acid, phthalic acid and the like.

Examples of carboxylic acid derivatives include β,β-dimethyl glutaric acid, barbituric acid, aminobutyric acid and the like.

Examples of hydroxycarboxylic acids include tartaric acid, citric acid, lactic acid and the like.

Examples of amino acids include aspartic acid, asparagine, glycine and the like.

Examples of amines include ethylenediamine, triethanolamine and the like.

Examples of imidazoles include imidazole, 5(4)-methylimidazole, 2,5 (4)-dimethylimidazole and the like.

Examples of salts of inorganic or organic acids are known in the art, including sodium and potassium salts.

Examples of buffer agents include 2-(N-morpholino) ethanesulfonic acid (MES), N-2-hydroxyethylpiperazine-N'-2-ethanesulfonic acid (HEPES), bis(2-hydroxyethyl) iminotris-(hydoxylmethyl)methane (Bistris), Tris, ADA, PIPES, Bistris-propane, ACES, MOPS, BES, TES, HEPES, HEPPS, Tricine, Bicine, glycylglycine, TAPS, CAPS and the like, which generally constitute a Good's buffer. Other useful buffers include Britton and Robinson's buffer and GTA buffer.

The above-listed inorganic acids, organic acids and their salts may be used alone or in combination. Also, the above-listed inorganic acids and organic acids may be used in combination.

The concentration of the buffer agent in the eluent is not particularly specified, so long as its buffer action is effective in water. It is preferably in the range of 0.1–1,000 mM, more preferably in the range of 1–500 mM.

The eluent may also contain (1) an inorganic salt, (2) a chaotropic ion, (3) a pH adjustor, (4) a water-soluble organic solvent and the like, which are listed below.

(1) Inorganic salt: Examples of inorganic salts include sodium chloride, potassium chloride, sodium sulfate, potassium sulfate, sodium phosphate and the like. While not particularly limited, they may preferably be incorporated in the amount of 1–1,500 mM.

(2) Chaotropic ion: Specific examples of chaotropic ions are listed in the subsequent description of an eluent E for use in the second invention. The concentration of the chaotropic ion in the eluent is preferably in the range of 0.1 mM–3,000 mM, more preferably in the range of 1 mM–1,000 mM, most preferably in the range of 10 mM–500 mM.

(3) pH adjustor: Known acids or bases may be used as pH adjustors. Examples of acids include hydrochloric acid, phosphoric acid, nitric acid, sulfuric acid and the like. Examples of bases include sodium hydroxide, potassium hydroxide, lithium hydroxide, magnesium hydroxide, barium hydroxide, calcium hydroxide and the like. While not limiting, these acids or bases may preferably be added in concentrations of 0.001–500 mM.

(4) Water-soluble organic solvent: Examples thereof include methanol, ethanol, acetonitrile, acetone and the like. Although not limiting, these organic solvents may preferably be added in concentrations of 0–80 % by volume. Preferably, their concetrations are maintained at levels insufficient to cause deposition of the chaotropic ion, inorganic acid, organic acid or any salt thereof used.

The second invention is now described.

In the second invention, at least two types of eluents are utilized including an eluent (referred to in this specification as "eluent E") which contains a chaotropic ion and also contains an inorganic acid, an organic acid and/or any salt thereof having a buffer capacity at a pH of 4.0–6.8, and an eluent (referred to in this specification as "eluent F") which contains an inorganic acid, an organic acid and/or any salt thereof having a buffer capacity at a pH of 6.5–8.0.

The eluent E contains a chaotropic ion. The chaotropic ion is produced via dissociation of compounds in an aqueous solution. It destroys a structure of water and suppresses the entropy reduction of water that occurs upon contact with a hydrophobic material. Examples of negative chaotropic ions include a tribromoacetate ion, trichloroacetate ion, thiocyanate ion, iodide ion, perchlorate ion, dichloro-acetate ion, nitrate ion, bromide ion, chloride ion, acetate ion and the like. Other examples are urea and the like. Examples of positive chaotropic ions include a barium ion, calcium ion, magnesium ion, lithium ion, cesium ion, potassium ion, guanidine ion and the like.

The use of the following chaotropic ions, among the above-listed ions, is preferred for their ability to improve separation precision; negative ions such as a tribromoacetate ion, trichloroacetate ion, thiocyanate ion, iodide ion, perchlorate ion, dichloro-acetate ion, nitrate ion and bromide ion; and positive ions such as a barium ion, calcium ion, magnesium ion, lithium ion, cesium ion and guanidine ion. Particularly preferred are a tribromoacetate ion, trichloroacetate ion, iodide ion, thiocyanate ion, perchlorate ion, nitrate ion and guanidine ion.

The concentration of the chaotropic ion present in the eluent E is preferably in the range of 0.1 mM–3,000 mM, more preferably in the range of 1 mM–1,000 mM, and most preferably in the range of 10 mM–500 mM. If it is below 0.1 mM, a separating effect may be reduced to result in the poor measurement precision. If it exceeds 3,000 mM, the effect of separating hemoglobins shows no further improvement. The above-listed chaotropic ions may be used alone or in combination.

The eluent E further contains an inorganic acid, an organic acid and/or any salt thereof having a buffer capacity at a pH of 4.0–6.8. Any of those listed in the preceding first invention as buffer agents, if having a buffer capacity at a pH of 4.0–6.8, can be used for such an inorganic acid, an organic acid and/or any salt thereof.

The concentration of the buffer agent in the eluent E is adjusted such that it exhibits a sufficient buffer action in water to maintain the eluent at a pH of 4.0–6.8. It is preferably in the range of 1 mM–1,000 mM, more preferably in the range of 10 mM–500 mM.

The eluent E is maintained at a pH of 4.0–6.8, preferably of 4.5–5.8. If a pH of the eluent E is below 4.0, denaturation of hemoglobin may be caused to occur. If it exceeds 6.8, hemoglobins may be charged less positively to reduce their tendencies to be retained by the cation exchange group, resulting in the reduced resolution.

The eluent F contains an inorganic acid, an organic acid and/or any salt thereof having a buffer capacity at a pH of 6.5–8.0, which are illustrated below.

Examples of inorganic acids include phosphoric acid and boric acid. Examples of organic acids include dicarboxylic acids, hydroxycarboxylic acids, amino acids, imidazoles, amines, alcohols and the like.

Examples of dicarboxylic acids include maleic acid, malonic acid, succinic acid and the like. Examples of hydroxycarboxylic acids include citric acid and the like. Examples of amino acids include asparagine, histidine and the like. Examples of imidazoles include 5(4)-hydroxy-imidazole, imidazole, 5(4)-methylimidazole, 2,5(4)-dimethyl-imidazole and the like. Examples of amines include ethylenediamine, diethanolamine, ethanolamine and the like.

Examples of alcohols include 2-amino-2-methyl-1,3-propanediol, 2-amino-2-ethyl-1,3-propanediol and the like.

Also useful are 2,4,6-collidine, N-ethylmorpholine, morpholine, 4-aminopyridine, pyrophosphoric acid, cacodylic acid, 5,5-diethyl barbituric acid, β, β'-dimethyl glutaric acid, glycerol phosphate and the like.

A Good's buffer is also useful, including MES, Bistris, ADA, PIPES, Bistris propane, ACES, BES, MOPS, TES, HEPES, HEPPS, Tris, Tricine, glycylglycine, Bicine, TAPS and the like, for example.

The salts of inorganic and organic acids are known in the art and include sodium salts, potassium salts and the like, for example.

The above-listed inorganic acids, organic acids and/or their salts may be used alone or in combination. The above-listed inorganic and organic acids may be used in combination.

The concentration of the buffer agent in the eluent F is adjusted such that it exhibits a sufficient buffer action in water to maintain the eluent at a pH of 6.5–8.0. It is preferably in the range of 1 mM–1,000 mM, more preferably in the range of 10 mM–500 mM.

The eluent F is maintained at a pH of 6.5–8.0, preferably of 6.7–7.8. This is because separation of hemoglobin $A_2$ becomes insufficient if the pH of the eluent F falls below 6.5 or exceeds 8.0.

Besides the eluents E and F, the second invention further uses an eluent (referred to in this specification as "eluent G") which has a lower pH and a higher salt concentration than the eluent F. The eluent G may be delivered to follow the eluent F.

The eluent G is preferably maintained at a pH lower than that of the eluent F by 0.1–5.0, more preferably by 0.5–4.0, most preferably by 1.0–3.0. Unless the pH of the eluent G is rendered at least 0.1 lower than that of the eluent F, poor separation of hemoglobin $A_2$ may result. Unless it is rendered at most 5.0 lower than that of the eluent F, denaturation of hemoglobin may be caused to occur, resulting in the poor hemoglobin measurement precision.

The eluent G is also maintained at a salt concentration higher than that of the eluent F. The salt concentration is represented in terms of a total concentration of cations present in each eluent. The eluent G is preferably maintained at a salt concentration higher than that of the eluent F by 0.5 mM–200 mM, more preferably by 1 mM–175 mM, most preferably by 5 mM–150 mM. Unless the salt concentration of the eluent G is rendered at least 0.5 mM higher than that of the eluent F, insufficient elution of hemoglobin $A_2$ may result. Unless it is rendered at most 200 mM higher than that of the eluent F, poor separation of hemoglobin $A_2$ may result.

The eluent G may contain, as a buffer agent, such an inorganic acid, organic acid and/or any salt thereof having a buffer capacity at a pH of 4.0–6.8 as incorporated in the eluent E. Preferably, a chaotropic ion may be added to the eluents F and G, as similar to the eluent E.

In the second invention, the eluent E, F or G may further contain (1) an inorganic salt, (2) a pH adjustor, (3) a water-soluble organic solvent, (4) a stabilizer, (5) amine, (6) a surfactant and the like, which are illustrated below.

Those additives described to be useful for the eluent in the first invention can also be used for (1) inorganic salt, (2) pH adjustor and (3) water-soluble organic solvent.

(4) Hemoglobin Stabilizer: Examples of stabilizers include chelating agents such as ethylenediaminetetraacetic acid (EDTA), and reducing agents/antioxidants such as glutathione.

(5) Amine: A primary purpose of amine addition is to suppress the nonspecific adsorption of hemoglobin. Useful amines are known in the art. The use of primary, secondary and tertiary amines having melecular weights of 20–500 is preferred.

(6) Surfactant: Examples of surfactants include nonionic, cationic and anionic surfactants. The use of the surfactant permits efficient hemolysis and is effective to clean a flow path through which a hemolyzed sample is passed during measurement such as by high-performance liquid chromatography (HPLC). Preferred among the above-listed surfactants are nonionic surfactants. Examples of nonionic surfactants include polyoxyethylenes (polyoxyethylene is hereinafter referred to as POE, and the number of moles of ethylene oxide added is represented by (n)), POE(7) decyl ether, POE(n) dodecyl ether, POE(10) tridecyl ether, POE(11) tetradecyl ether, POE(n) cetyl ether, POE(n) stearyl ether, POE(n) oleyl ether, POE(17) cetylstearyl ether, POE(n) octyl phenyl ether, POE(n) nonylphenyl ether, sorbitan mono-laurate, sorbitan monopalmitate, sorbitan monostearate, sorbitan monooleate, POE(n) sorbitan monolaurate, POE(n) sorbitan monopalmitate, POE(n) sorbitan monostearate, POE(n) sorbitan monooleate and the like.

The above-listed surfactants may be used alone or in combination. Preferably, these surfactants may be added in the amount of 0.01–10 % by weight.

The constitution common to the first and second inventions (hereinafter referred to as "present invention", collectively) is now described.

In the present invention, an eluent (referred to in this specification as eluent "H") at a pH of 6.8–12 is preferably delivered for the primary purpose of cleaning a column. The pH of the eluent H is such specified because of the following reasons. If below 6.8, the eluent H while passed through the column may fail to reach a pH equal to an isoelectric point of hemoglobin, resulting in the failure to clean the column effectively. If above 12, decomposition of a packing material may be caused to occur. More preferably, the eluent H is maintained at a pH of 7.5–11. The pH range of 8.0–9.5 is particularly preferred. However, the pH of the eluent H may be permitted to exceed 12, in the case where measurement is unaffected by decomposition of a packing material.

The eluent H may comprise, for example, a buffer containing an inorganic acid or its salt such as phosphoric acid, boric acid and carbonic acid; hydroxycarboxylic acid such as citric acid; carboxylic acid derivative such as β,β-dimethylglutaric acid; dicarboxylic acid such as maleic acid; or an organic acid or its salt such as cacodylic acid.

Examples of buffers include 2-(N-morpholino) ethanesulfonic acid (MES), N-2-hydroxyethylpiperazine-N'-2-ethanesulfonic acid (HEPES), bis(2-hydroxyethyl) iminotris-(hydoxylmethyl)methane (Bistris), Tris, ADA, PIPES, Bistris-propane, ACES, MOPS, BES, TES, HEPES, HEPPS, Tricine, Bicine, glycylglycine, TAPS, CAPS and the like, which generally constitute a Good's buffer. Other useful buffers include Britton and Robinson's buffer and GTA buffer. Also useful are organic substances, including imidazoles such as imidazole; amines such as diethanolamine and triethanol-amine; amino acids such as glycine and the like. These inorganic acids, organic acids and their salts may be used in combination. Alternatively, such inorganic and organic acids may be used in combination.

The above-listed inorganic acids., organic acids and their salts may be incorporated in the eluent H within the concentration range that allows them to exhibit sufficient buffer actions in water to keep the eluent H at a pH of at least 6.8, i.e., preferably within the concentration range of 1 mM–1, 000 mM, more preferably of 10 mM–500 mM.

Preferably, a chaotropic ion may preferably be added to the eluent H to achieve a more effective column cleaning. Useful chaotropic ions are listed above. The chaotropic ion concentration is preferably in the range of 1 mM–3,000 mm, more preferably in the range of 10 mM–1,000 mM, most preferably in the range of 50 mM–500 mM.

Like the above-described eluents E, F and G, the eluent H may further contain various additives, including, for example, (1) an inorganic salt, (2) a pH adjustor, (3) a water-soluble organic solvent, (4) a stabilizer, (5) amine, (6) a surfactant and the like.

In the first invention, in the case where the eluent H is used, the eluents may be delivered in the order of A, B and H, or in the order of A, B, D and H, or in the order of A, B, C, D and H. In the second invention, in the case where the eluent H is used, the eluents may be delivered in the order of E, F and H, or in the order of E, F, G and H.

Also in the present invention, it is more preferred that an azide ion be added to at least one eluent selected from the eluents A–H. This azide ion may be added to a hemolyzing solution. The azide ion may be added to either or both of the eluent and hemolyzing solution. The azide ion may be added in the form of its salt which dissociates in an aqueous solution to produce azide ions. Useful azide salts are known in the art. The use of sodium azide, barium azide or the like is preferred.

The azide ion concentration in the eluent or hemolysed solution is preferably in the range of 0.001–0.5 % by weight, more preferably in the range of 0.005–0.4 % by weight. If the concentration is below 0.001 % by weight, an effect of improving resolution can not be obtained. If it exceeds 0.5 % by weight, no further resolution improvement can not be expected.

A packing material, for use in the cation exchange liquid chromatography according to the present invention, comprises particles having at least one type of cation exchange group. Such particles can be prepared, for example, by introducing cation exchange groups into polymer particles.

Examples of cation exchange groups are known in the art, and include a carboxyl group, a sulfonic acid group, a phosphoric acid group and the like. Any combination of such cation exchange groups may be introduced.

Preferably, a packing material is utilized having at least one type of strong cation exchange group. This strong cation exchange group refers to a cation exchange group which exhibits an ion exchange action even in an eluent maintained at an approximate pH of 2–3, such as a sulfonic acid group among those listed above. The use of the packing material having at least one strong cation exchange group reduces an eluent pH to such a degree that allows hemoglobins to be charged more positively and increases their tendency to be retained by a column, resulting in the increased resolution.

The above-described particles have diameters preferably in the range of 0.1–20 μm, more preferably in the range of 0.2–8 μm. The particle size distribution is preferably 40% or less, more preferably 30% or less, when represented by a coeffeicient of variation (CV value)(=(a standard deviation of a particle size distibution)/(its arithmetic mean)×100 (%))

Examples of such polymer particles include inorganic particles such as silica and zirconia; natural polymer particles such as cellulose, polyamino acid and chitosan; synthetic polymer particles such as polystyrene and polyacrylate; and the like.

Preferably, the polymer particle constituents, other than the introduced cation exchange group, are relatively hydrophilic. In view of the resistance to pressure and swelling, those constituents preferably have higher crosslinking levels.

A cation exchange group can be introduced into polymer particles by any known technique. For example, a technique can be utilized which comprises, in sequence, preparing polymer paticles having functional groups (such as hydroxyl, amino, carboxyl and epoxy) and allowing the functional groups to undergo a chemical reaction so that cation exchange groups are introduced into the polymer particles.

Alternatively, a cation exchange packing material may be prepared by a technique that produces polymer particles via polymerization of a monomer having a cation exchange group. For example, a technique can be utilized which involves mixing a cation exchange group-containing monomer with a crosslinking monomer and allowing the mixture to polymerize in the presence of a polymerization initiator.

Another applicable technique encompasses mixing polymerizable ester containing a cation exchange group, such as methyl (meth)acrylate and ethyl (meth)acrylate, with a crosslinking monomer; allowing the mixture to polymerize in the presence of a polymerization initiator; and subjecting the resulting polymer particles to hydrolysis so that the ester is converted into a cation exchange group.

Japanese Patent Publication No. Hei 8-7197 discloses a further applicable technique which comprises, in sequence, preparing crosslinked polymer particles, adding thereto a cation exchange group-containing monomer, and allowing the monomer to polymerize in the vicinity of polymer particle surfaces.

The above-described packing material is packed into a column for use in the liquid chromatographic measurement. The column is preferably sized to have an inner diameter of 0.1–50 mm and a length of 1–300 mm. More preferably, it measures an inner diameter of 0.2–30 mm and a length of 5–200 mm. If the column measures below 0.1 mm in inner diameter and below 1 mm in length, poor operability and resolution results. On the other hand, if the column measures above 50 mm in internal diameter and above 300 mm in length, the increased amount of packing material is required. Poor resolution also results.

Although any known technique can be utilized for packing the material into a column, the use of a slurry packing technique is preferred. Illustrating a specific example, packing material particles are dispersed in a buffer, such as an eluent, to provide a slurry which is subsequently injected into a column as by a delivery pump.

The column can be formed from materials known in the art, including metals such as stainless steel, glasses, resins such as PEEK (polyether ether ketone), and the like. Preferably, a portion of the column, e.g., an inner surface, that contacts with packing materials may be covered with an inert material. Examples of such inert materials include PEEK, polyethylene, Teflon, titanium compounds, silicon compounds, silicone films.

The column may be used in combination with a filter or a prefilter at least surface of which is formed from an inert material. Examples of such inert materials include cellulose ester, cellulose acetate, cellulose triacetate, cellulose, cellulose nitrate, polytetrafluoroethylene, polyvinylidene difluoride, polysulfone, polyethylene, polyether ether ketone, polyether sulfone, polypropylene, nylon, polyvinylidene fluoride, glass materials, acrylic copolymers, oxide ceramics, carbide ceramics, nitride ceramics, silicide ceramics, boride ceramics, titanium and the like. These materials can be used in any suitable combination. In the case where stainless steel and other materials are used which are not inert in nature, a suitable technique may be utilized whereby they are covered with an inert material, or they are rendered inert as by a treatment with silicone, or they are blocked with a blocking agent such as bovine serum albumin, gelatin, casein, globulin or hemoglobin.

Liquid chromatography for use in the separation method of the present invention is known in the art, and generally employs a delivery pump, a sample injecting equipment (sampler), a column and a detector. Other suitable auxiliary equipments (such as a column oven and an eluent degasser) may also be attached.

In the present invention, for liquid chromatography, a semimicro system can be used including liquid contacting parts, e.g., a pump, a mixing column, a sampler, pipings, a prefilter (holder, filter), a column and a detector (cell), which are reduced in dead volume to the minimum. The mixing column is preferably reduced in size to less than 500 μl, more preferably to less than 250 μl. An injection valve for the sampler is preferably reduced in volume to less than 10 μl, more preferably to less than 5 μl, most preferably to less than 2 μl. An inner diameter of the piping is preferably reduced to less than 0.25 mm, more preferably to less than 0.13 mm, most preferably to less than 0.065 mm. In the case where the sampler, prefilter, column, detector and the like are connected by pipings, such pipings are preferably reduced in length to the minimum. The detector (cell) is preferably reduced in volume to less than 20 μl, more preferably to less than 10 μl, most preferably to less than 5 μl The delivery pump preferably has the ability to supply a stable flow with least pulsation. More precise separation can be achieved within a short period of time when the liquid contacting parts are formed from inert materials, such as Teflon and PEEK, and an interior dead volume of the equipment is minimized.

Figure 1:
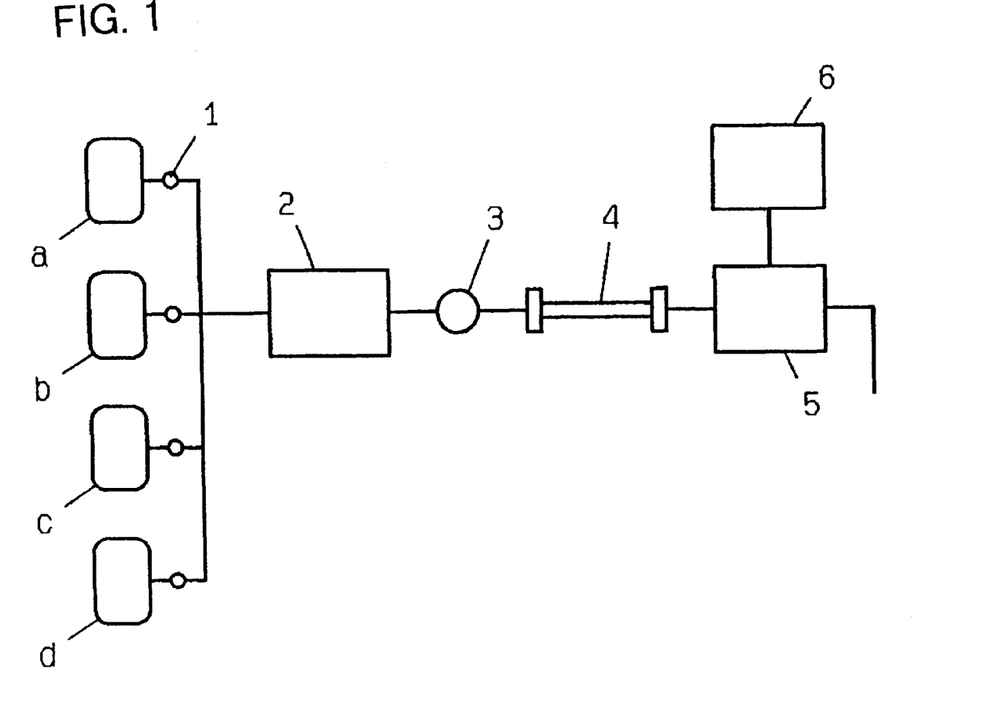
FIG. 1 shows an exemplary construction of a liquid chromatograph.

An exemplary construction of the liquid chromatograph used to perform separation according to a stepwise gradient elution technique is shown in FIG. 1. Eluents a, b, c and d have differing elution powers. A solenoid valve 1 is opened at a specific time interval to allow deliver of each eluent. The eluent and a sample from a sample injection port 3 are fed together into a column 4 by the action of a delivery pump 2. Various components present in the sample are detected by a detector 5. An area, height and others of each peak are calculated by an integrator 6.

Other conditions for use in the separation method of the present invention are known in the art. Each eluent is preferably delivered at a flow rate of 0.05–5 ml/min, more preferably of 0.2–3 ml/min. In the case where the above-described semimicro equivalent system is used, each eluent is preferably delivered at a flow rate of 0.001–3 ml/min, more preferably of 0.01–1.8 ml/min, further preferably of 0.03–1 ml/min. It is difficult to stabilize the flow rate if slower than 0.001 ml/min. If the flow rate exceeds 3 ml/min, the separation precision may be lowered.

Various techniques, without limitation, can be utilized to deliver an eluent for use in the separation method of the present invention, including a linear gradient elution technique and a stepwise gradient elution technique, for example.

While not particularly limited, the detection of hemoglobins is preferably performed by a 415 nm visible light.

The hemoglobin mixture to be separated by the present method is generally prepared by diluting a hemolyzed solution obtained via hemolysis with a hemolytically active substance such as a surfactant. The amount of the hemoglobin mixture injected to the liquid chromatograph is varied depending upon the dilution ratio, but is preferably in the approximate range of 0.1–100 μl.

BEST MODE FOR CARRYING OUT THE INVENTION

The present invention is below described in detail with reference to non-limiting Examples and Comparative Examples.

EXAMPLE 1

Preparation of Packing Material 2 g of benzoyl peroxide (product of Wako Jyunyaku Co., Ltd.) was allowed to dissolve in a mixture containing 450 g of tetraethylene glycol dimethacrylate (product of Shin-Nakamura Chem. Co., Ltd.) and 50 g of 2-hydroxy-1,3-dimethacryloxypropane (product of Wako Jyunyaku Co., Ltd.). The resulting mixture was dispersed in 2,500 mL of a 4 wt. % aqueous solution of polyvinyl alcohol (product of Nippon Gosei Chem. Co., Ltd.), heated with agitation under a nitrogen atmosphere to 80° C. and then allowed to polymerize for 1.5 hours. The reaction system was then cooled to 35 C . Thereafter, 400 g of a 50 % aqueous solution of 2-acrylamide-2-methylpropanesulfonic acid (product of Tokyo Kasei Co., Ltd.) and 400 ml of methanol were added to the reaction system which was again heated with agitation to 80 C. and then allowed to polymerize for 1.3 hours. The polymerizate was washed, dried and classified to obtain particles with a mean particle diameter of 6.5 μm.

Packing of the Material into a Column

The particles obtained were packed into a column according to the following procedure.

0.7 g of the above-obtained particles was dispersed in 30 mL of a 50 mM phosphate buffer (pH 5.8), subjected to an ultrasonic treatment for 5 minutes and stirred well. The whole content was injected into a packer (product of Umetani Seiki Co., Ltd.) connected to a vacant stainless steel column (inner diameter 4.6 φ×35 mm). The content was packed under a constant pressure of 300 kg/cm$^2$ into the column by a delivery pump (product of Sanuki Ind. Co., Ltd.) connected thereto.

Using the packed column, hemoglobin $A_2$ was separated and measured under the following conditions.

Measurement Conditions

System: delivery pump: LC-9A (manufactured by Shimadzu Seisakusho Co., Ltd.)
autosampler: ASU-420 (manufactured by Sekisui Chem. Ind. Co., Ltd.)
detector: SPD-6AV (manufactured by Shimadzu Seisakusho Co., Ltd.)

Eluents: eluent A: 170 mM phosphate buffer (pH 5.7)
eluent B: 130 mM phosphate buffer (pH 7.0)
eluent H: 300 mM phosphate buffer (pH 8.5)

During measurement, the elunt A was delivered for the initial 1-minute period, the eluent B for the next 1-minute period, the eluent H for the next 0.2-minute period and again the eluent A for the final 0.8-minute period.

Flow rate: 1.0 ml/min
Detection wavelength: 415 nm
Sample injection: 10 μl

Measurement Sample 1

Blood was collected from a healthy human and 10 mg/ml of sodium fluoride, as an anticoagulant, was added. A 150-fold amount of a hemolyzing solution (consisting of 0.1 wt. % polyethylene glycol mono-4-octylphenyl ether (Triton X-100, manufactured by Tokyo Kasei Co., Ltd.) and a 20 mM phosphate buffer (pH 7.0)) was added thereto to cause hemolysis, so that a measurement sample was obtained.

Measurement Sample 2

Lyphocheck $HbA_2$ Control-Level 2 (product of Bio-Laboratories Inc.) was allowed to dissolve in 1 ml water and then diluted with an 100-fold amount of the hemolyzing solution to thereby obtain a measurement sample.

Measurement Results

Figure 2:
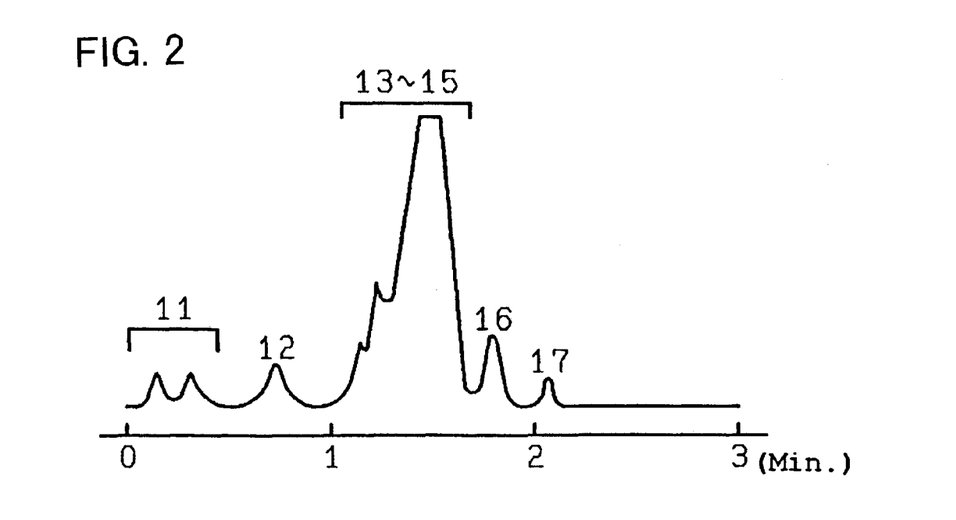
FIG. 2 shows a chromatogram obtained when separation of hemoglobin $A_2$ (sample 1) was carried out under the measurement conditions of Example 1.

The chromatogram obtained when measurement of the sample 1 was performed under the above-specified conditions is shown in FIG. 2. Peak 11 represents $HbA_{1a}$ and $HbA_{1b}$. Peak 12 represents HbF. Peak 13 represents labile $HbA_{1c}$. Peak 14 represents stable $HbA_{1c}$. Peak 15 represents $HbA_0$. Peak 16 represents $HbA_2$ and Peak 17 represents other Hb's.

As can be seen from the result shown in FIG. 2, $HbA_2$ (Peaks 16) is separated in a satisfactory manner.

Measurement was repeated ten times for each of the samples 1 and 2. The $A_2$ peak areas (%) measured and the measurement precision thereof (SD: standard deviation, CV (%): coeffecient of variation) calculated for each sample are listed in Table 1. As can be seen from the results, both of the samples 1 and 2 were measured with a satisfactory consistency.

Then, 3,000 specimens were serially measured for the sample 1. The retention time of $HbA_2$ is shown in Table 2 for every 500th specimen. As can be seen from the results, the change in percentage of retention time is very small.

The percentage change=($A_2$ retention time at the first measurement–$A_2$ retention time at the 3,000th measurement)/($A_2$ retention time at the first measurement)× 100.

TABLE 1

| | Sample 1 | | | | Sample 2 | | | |
|---|---|---|---|---|---|---|---|---|
| | Ex. 1 | Ex. 2 | Comp. Ex. 1 | Comp. Ex. 2 | Ex. 1 | Ex. 2 | Comp. Ex. 1 | Comp. Ex. 2 |
| 1 | 2.2 | 2.2 | 2.4 | 2.2 | 4.5 | 4.5 | 4.4 | 4.3 |
| 2 | 2.3 | 2.2 | 2.3 | 2.3 | 4.5 | 4.5 | 4.2 | 4.3 |
| 3 | 2.2 | 2.2 | 2.0 | 2.1 | 4.6 | 4.6 | 4.0 | 4.6 |
| 4 | 2.2 | 2.3 | 2.3 | 2.2 | 4.3 | 4.5 | 4.3 | 4.3 |
| 5 | 2.3 | 2.2 | 2.4 | 2.4 | 4.6 | 4.6 | 4.7 | 4.6 |
| 6 | 2.2 | 2.2 | 2.1 | 2.2 | 4.4 | 4.5 | 4.3 | 4.4 |

TABLE 1-continued

| | Sample 1 | | | | Sample 2 | | | |
|---|---|---|---|---|---|---|---|---|
| | Ex. 1 | Ex. 2 | Comp. Ex. 1 | Comp. Ex. 2 | Ex. 1 | Ex. 2 | Comp. Ex. 1 | Comp. Ex. 2 |
| 7 | 2.3 | 2.2 | 2.2 | 2.3 | 4.6 | 4.6 | 4.2 | 4.7 |
| 8 | 2.1 | 2.3 | 2.2 | 2.2 | 4.5 | 4.5 | 4.5 | 4.5 |
| 9 | 2.2 | 2.2 | 2.1 | 2.4 | 4.4 | 4.4 | 4.8 | 4.1 |
| 10 | 2.2 | 2.2 | 2.0 | 2.1 | 4.4 | 4.4 | 4.2 | 4.2 |
| Mean | 2.2 | 2.2 | 2.2 | 2.3 | 4.5 | 4.5 | 4.4 | 4.4 |
| SD | 0.06 | 0.04 | 0.15 | 0.11 | 0.10 | 0.07 | 0.25 | 0.19 |
| CV % | 2.8 | 1.9 | 6.7 | 4.8 | 2.3 | 1.6 | 5.6 | 4.4 |

TABLE 2

| Numbers of specimens | Ex. 1 | Ex. 2 | Comp. Ex. 1 | Comp. Ex. 2 |
|---|---|---|---|---|
| 1 | 1.8 | 1.8 | 14.5 | 3.7 |
| 500 | 1.8 | 1.8 | 14.3 | 3.6 |
| 1000 | 1.8 | 1.8 | 14.0 | 3.5 |
| 1500 | 1.8 | 1.8 | 13.5 | 3.5 |
| 2000 | 1.7 | 1.8 | 13.0 | 3.4 |
| 2500 | 1.7 | 1.7 | 12.8 | 3.3 |
| 3000 | 1.7 | 1.7 | 12.5 | 3.2 |
| % Change | 5.6 | 5.6 | 13.8 | 13.5 |

Retention Time (Min.)

EXAMPLE 2

Separation and measurement of hemoglobin $A_2$ were carried out under the same conditions as in Example 1, with the exception that the following eluents and elution conditions were used.

Eluents: eluent A: 170 mM phosphate buffer (pH 5.7)

eluent B: 130 mM phosphate buffer (pH 7.5)

eluent C: 170 mM phosphate buffer (pH 5.7)

eluent D: 240 mM phosphate buffer (pH 6.5)

eluent H: 300 mM phosphate buffer (pH 8.5)

During measurement, the elunt A was delivered for the initial 1-minute period, the eluent B for the next 0.4-minute period, the eluent C for the next 0.2-minute period, the eluent D for the next 0.4-minute period, the eluent H for the next 0.2-minute period and again the eluent A for the final 0.8-minute period.

Figure 3:
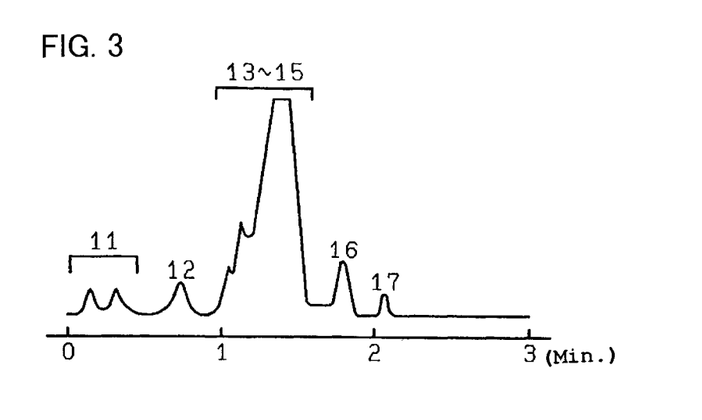
FIG. 3 shows a chromatogram obtained when separation of hemoglobin $A_2$ (sample 1) was carried out under the measurement conditions of Example 2.

The chromatogram obtained when measurement of the sample 1 was performed under the above-specified conditions is shown in FIG. 3. As can be seen from the result shown in FIG. 3, $HbA_2$ (Peak 16) is separated in a satisfactory manner. The measurement precision and the change in percentage of retention time are shown in Table 1 and Table 2, respectively. As can be seen from the results, both the measurement variation and the change in percentage of retention time were small, thereby demonstrating that the measurement was carried out in a satisfactory manner.

COMPARATIVE EXAMPLE 1

Separation and measurement of hemoglobins were carried out under the same conditions as in Example 1, with the exception that the following eluents and elution conditions were used.

Eluents: eluent 1: 170 mM phosphate buffer (pH 5.7)

eluent 2: 300 mM phosphate buffer (pH 5.7)

During measurement, the eluent 1 was delivered for the initial 14.5-minute period, the eluent 2 for the subsequent 0.7-minute period and again the eluent 1 for the final 0.8-minute period.

Figure 4:
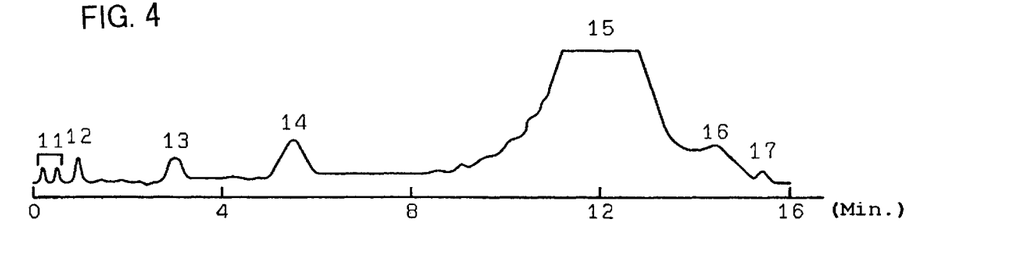
FIG. 4 shows a chromatogram obtained when separation of hemoglobin $A_2$ (sample 1) was carried out under the measurement conditions of Comparative Example 1.

The chromatogram obtained when measurement of the sample 1 was performed under the above-specified conditions is shown in FIG. 4. Notwithstanding the extended measurement time, the results revealed poor separation of $HbA_2$ (Peak 16). The measurement precision and the change in percentage of retention time are shown in Table 1 and Table 2, respectively. As can be seen from the results, the measurement variation and the change in percentage of retention time both increased.

COMPARATIVE EXAMPLE 2

Separation and measurement of hemoglobins were carried out under the same conditions as in Example 1, with the exception that the following eluents and elution conditions were used.

Eluents: eluent 1: 170 mM phosphate buffer (pH 5.7)

eluent 2: 250 mM phosphate buffer (pH 5.7)

eluent 3: 300 mM phosphate buffer (pH 5.7)

During measurement, the eluent 1 was delivered for the initial 1-minute period, the eluent 2 for the next 2.5-minute period, the eluent 3 for the next 0.7-minute period and again the eluent 1 for the final 0.8-minute period.

Figure 5:
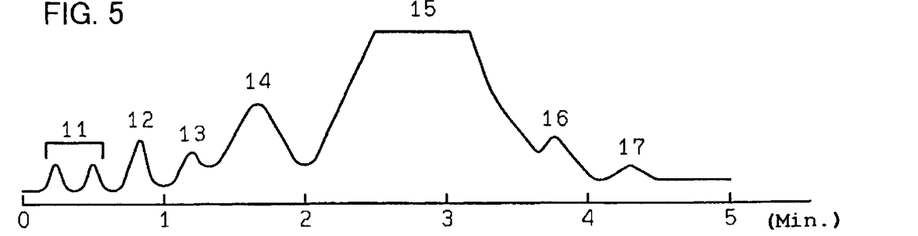
FIG. 5 shows a chromatogram obtained when separation of hemoglobin $A_2$ (sample 1) was carried out under the measurement conditions of Comparative Example 2.

The chromatogram obtained when measurement of the sample 1 was performed under the above-specified conditions is shown in FIG. 5. The results reveal poor separation of $HbA_2$ (Peak 16). The measurement precision and the change in percentage of retention time are shown in Table 1 and Table 2, respectively. As can be seen from the results, the measurement variation and the change in percentage of retention time both increased.

EXAMPLE 3

Measurement of the sample 1 was carried out under the same conditions as in Example 1, except that the following eluents and elution conditions were used.

Eluents: eluent A1: 50 mM phosphate buffer containing 45 mM perchloric acid (pH 5.3)

eluent A2: 50 mM phosphate buffer containing 55 mM perchloric acid (pH 5.3)

eluent B: 18 mM phosphate buffer (pH 7.2)

eluent D: 125 mM phosphate buffer (pH 5.7)

eluent H: 300 mM phosphate buffer (pH 8.5)

During measurement, the elunt A1 was delivered for the initial 1-minute period, the eluent $A_2$ for the next 0.5-minute period, the eluent B for the next 0.6-minute period, the eluent D for the next 0.4 minute period, the eluent H for the next 0.2-minute period and again the eluent A1 for the final 0.8-minute period.

Flow rate: 2.0 ml/min

Figure 6:
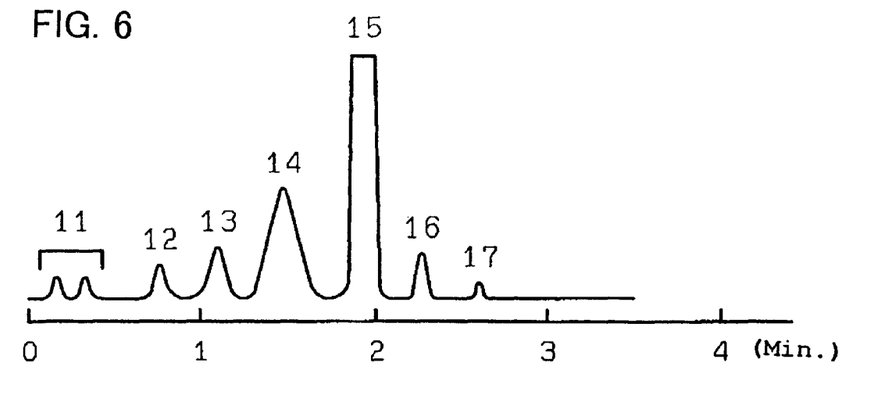
FIG. 6 shows a chromatogram obtained when separation of hemoglobin $A_2$ (sample 1) was carried out under the measurement conditions of Example 3.

The chromatogram obtained is shown in FIG. 6. The results reveal satisfactory separation of $HbA_2$ (Peak 16) and stable $HbA_{1c}$ (Peak 14).

EXAMPLE 4

Measurement of the following sample 3 was carried out under the same conditions as in Example 1, except that the below-specified eluents and elution conditions were used.

Measurement Sample 3

AFSC Control (product of Helena Laboratories Inc.) was diluted with a 67-fold amount of the hemolyzing solution to thereby obtain a measurement sample.

Measurement Conditions

Eluents: eluent A1: 50 mM phosphate buffer containing 45 mM perchloric acid and 0.03 wt. % sodium azide (pH 5.3)

eluent $A_{2}$: 50 mM phosphate buffer containing 55 mM perchloric acid (pH 5.3)

eluent B: 18 mM phosphate buffer (pH 7.2)

eluent D1: 125 mM phosphate buffer (pH 5.7)

eluent D2: 150 mM phosphate buffer (pH 5.7)

eluent H: 300 mM phosphate buffer (pH 8.5)

During measurement, the elunt Al was delivered for the initial 1-minute period, the eluent $A_2$ for the next 0.5-minute period, the eluent B for the next 0.6-minute period, the eluent $D_1$ for the next 0.4-minute period, the eluent D2 for the next 0.5-minute period, the eluent H for the next 0.2-minute period and again the eluent Al for the final 0.8-minute period.

Flow rate: 2.0 ml/min

Figure 7:
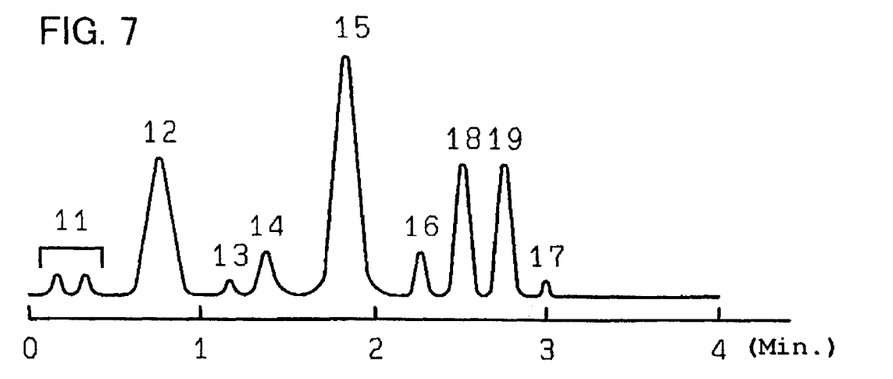
FIG. 7 shows a chromatogram obtained when separation of hemoglobin $A_2$ (sample 3) was carried out under the measurement conditions of Example 4.

The chromatogram obtained is shown in FIG. 7. The results reveal satisfactory separation of $HbA_2$ (Peak 16), HbS (Peak 18) and HbC (Peak 19).

COMPARATIVE EXAMPLE 3

Measurement of the sample 3 was carried out under the same conditions as in Example 4, except that the following eluents and elution conditions were used.

Eluents: eluent 1: 50 mM phosphate buffer containing 45 mM perchloric acid and 0.03 wt. % sodium azide (pH 5.3)

eluent 2: 50 mM phosphate buffer containing 55 mM perchloric acid (pH 5.3)

eluent 3: 18 mM phosphate buffer (pH 7.2)

eluent 4: 35 mM phosphate buffer (pH 7.2)

eluent 5: 40 mM phosphate buffer (pH 7.2)

eluent 6: 300 mM phosphate buffer (pH 8.5)

During measurement, the elunt 1 was delivered for the initial 1-minute period, the eluent 2 for the next 0.5-minute period, the eluent 3 for the next 0.6-minute period, the eluent 4 for the next 0.4-minute period, the eluent 5 for the next 0.5-minute period, the eluent 6 for the next 0.2-minute period and again the eluent 1 for the final 0.8-minute period.

Figure 8:
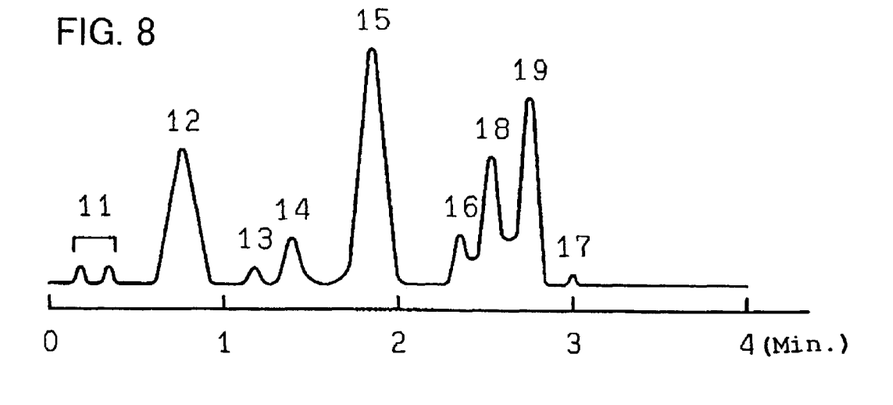
FIG. 8 shows a chromatogram obtained when separation of hemoglobin $A_2$ (sample 3) was carried out under the measurement conditions of Comparative Example 3.

The chromatogram obtained is shown in FIG. 8. The results reveal that $HbA_2$ (Peak 16), HbS (Peak 18) and HbC (Peak 19) are separated poorly from each other.

EXAMPLE 5

Preparation of Packing Material 2 g of benzoyl peroxide (product of Wako Jyunyaku Co., Ltd.) was allowed to dissolve in a mixture containing 450 g of tetraethylene glycol dimethacrylate (product of Shin-Nakamura Chem. Co., Ltd.) and 50 g of 2-hydroxy-1,3-dimethacryloxypropane (product of Wako Jyunyaku Co., Ltd.). The resulting mixture was dispersed in 2,500 mL of a 4 wt. % aqueous solution of polyvinyl alcohol (product of Nippon Gosei Chem. Co., Ltd.), heated with agitation under a nitrogen atmosphere to 80° C. and then allowed to polymerize for 1.5 hours. The reaction system was then cooled to 35 C. Thereafter, 400 g of a 50% aqueous solution of 2-acrylamide-2-methylpropanesulfonic acid (product of Tokyo Kasei Co., Ltd.) and 400 ml of methanol were added to the reaction system which was again heated with agitation to 80° C. and then allowed to polymerize for 1.3 hours. The polymerizate was washed, dried and classified to obtain particles with a mean particle diameter of 6.5 μm.

Packing of the Material into a Column

The particles obtained were packed into a column according to the following procedure.

0.7 g of the above-obtained particles was dispersed in 30 mL of a 50 mM phosphate buffer (pH 5.8), subjected to an ultrasonic treatment for 5 minutes and stirred well. The whole content was injected into a packer (product of Umetani Seiki Co., Ltd.) connected to a vacant stainless steel column (inner diameter 4.6×35 mm). The content was packed under a constant pressure of 300 kg/cm² into the column by a delivery pump (product of Sanuki Ind. Co., Ltd.) connected thereto.

Using the packed column, separation and measurement of hemoglobin $A_2$ were carried out under the following conditions.

Measurement Conditions

System: delivery pump: LC-9A (manufactured by Shimadzu Seisakusho Co., Ltd.)

autosampler: ASU-420 (manufactured by Sekisui Chem. Ind. Co. Ltd.)

detector: SPD-6AV (manufactured by Shimadzu Seisakusho Co., Ltd.)

Eluents: eluent E: 50 mM phosphate buffer containing 45 mM perchloric acid (pH 5.3)

eluent F: 25 mM tris(hydroxymethyl) amino-methane buffer (pH 7.5) eluent H: 50 mM phosphate buffer containing 200 mM perchloric acid (pH 8.5)

During measurement, the eluent E was delivered for the initial 1.7-minute period, the eluent F for the next 1.8-minute period, the eluent H for the next 0.1-minute period and again the eluent E for the final 0.4-minute period.

Flow rate: 2.0 ml/min

Detection wavelength: 415 nm

Sample injection: 10 μl

Measurement Sample 4

Blood was collected from a healthy human and 10 mg/ml of sodium fluoride, as an anticoagulant, was added. A 150-fold amount of a hemolyzing solution (phosphate buffer (pH 7) containing, as a surfactant, 0.1 wt. % polyethylene glycol mono-4-octylphenyl ether (Triton X-100, manufactured by Tokyo Kasei Co., Ltd.) was added thereto to cause hemolysis, thereby obtaining a measurement sample 4.

Measurement Sample 5: CHb-containing Sample 1 ml of a 0.3 wt. % sodium cyanate solution in saline was added to 10 ml healthy human blood. The mixture was allowed to react at 37 C. for 3 hours, then subjected to hemolysis by the aforementioned hemolyzing solution and diluted 150-fold to obtain a measurement sample 5.

Measurement Sample 6: AHb-containing Sample 1 ml of a 0.3 wt. % acetaldehyde solution in saline was added to 10 ml healthy human blood. The mixture was allowed to react at 37 C. for 3 hours, then subjected to hemolysis by the aforementioned hemolyzing solution and diluted 150-fold to obtain a measurement sample 6.

Measurement Results

Figure 9:
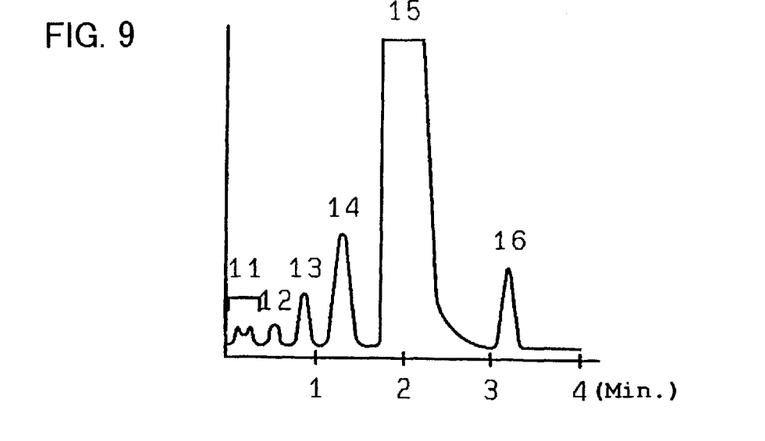
FIG. 9 shows a chromatogram obtained when separation of hemoglobin $A_2$ (sample 4) was carried out under the measurement conditions of Example 5.
Figure 10:
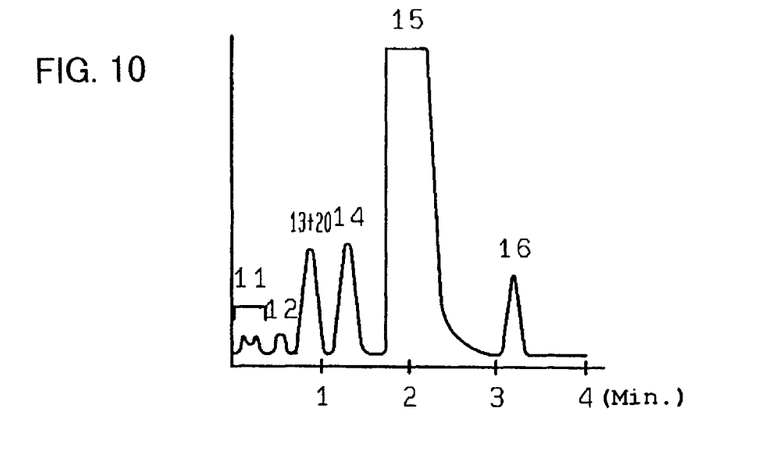
FIG. 10 shows a chromatogram obtained when separation of hemoglobin $A_2$ (sample 5) was carried out under the measurement conditions of Example 5.
Figure 11:
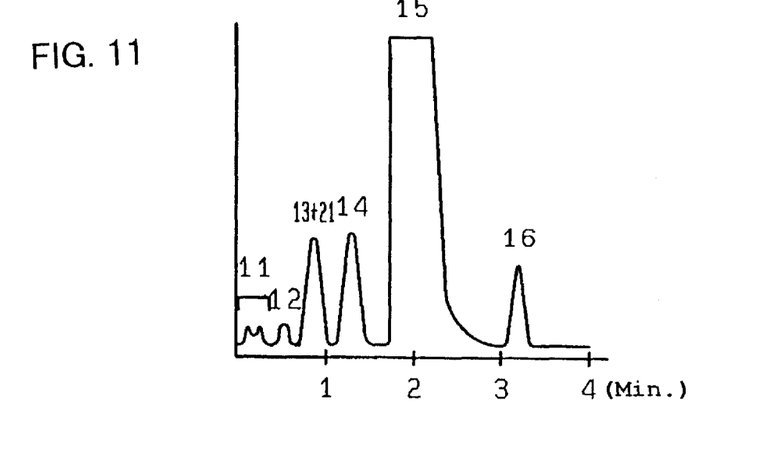
FIG. 11 shows a chromatogram obtained when separation of hemoglobin $A_2$ (sample 6) was carried out under the measurement conditions of Example 5.

The chromatograms obtained when measurement of the samples 4, 5 and 6 were performed under the above-specified conditions are shown in FIGS. 9–11. FIG. 9 shows the results obtained for the sample 4, FIG. 10 for the sample 5 and FIG. 11 for the sample 6. Peak 11 represents $HbA_{1a}$ and $HbA_{1b}$. Peak 12 represents HbF. Peak 13 represents labile $HbA_{1c}$. Peak 14 represents stable $HbA_{1c}$. Peak 15 represents $HbA_0$. Peak 16 represents $HbA_2$. Peaks 20 and 21 represent CHb and AHb, respectively. As can be seen from the result shown in FIG. 9, the separation of stable $HbA_{1c}$ (Peak 14) and $HbA_2$ (Peak 16) was achieved in a satisfactory manner. In FIG. 10, CHb (Peak 20) is well separated from stable $HbA_{1c}$ (Peak 14). In FIG. 11, AHb (Peak 21) is well separated from stable $HbA_{1c}$ (Peak 14). Also, $HbA_2$ (Peak 16) is separated in a satisfactory manner.

EXAMPLE 6

Measurement of hemoglobins was carried out under the same conditions as in Example 5, except that the eluents were used having the following compositions.

Eluents: eluent E: 25 mM succinate-20 mM phosphate buffer containing 50 mM perchloric acid (pH 5.3)

eluent F: 25 mM tris(hydroxymethyl) amino-methane buffer (pH 7.5)

eluent H: 20 mM succinate-20 mM phosphate buffer containing 250 mM perchloric acid (pH 8.4)

Following Example 5, the measurement samples 4, 5 and 6 were used. Good results were obtained as similar to Example 5.

EXAMPLE 7

Measurement of the samples 4, 5 and 6 were carried out in the same manner as in Example 6, with the exception that the eluent F was used having the following composition.

Eluent F: 40 mM Bistris buffer (pH 7.8)

EXAMPLE 8

Measurement of the samples 4, 5 and 6 were carried out in the same manner as in Example 6, with the exception that the eluent F was used having the following composition.

Eluent F: 40 mM TES buffer (pH 7.5)

EXAMPLE 9

Measurement of the samples 4, 5 and 6 were carried out in the same manner as in Example 6, with the exception that the eluent F was used having the following composition.

Eluent F: 15 mM phosphate buffer (pH 7.1)

EXAMPLE 10

Measurement of the samples 4, 5 and 6 were carried out in the same manner as in Example 6, with the exception that the eluent F was used having the following composition.

Eluent F: 40 mM Bicine buffer (pH 7.6)

EXAMPLE 11

Measurement of the samples 4, 5 and 6 were carried out in the same manner as in Example 6, with the exception that the eluent F was used having the following composition.

Eluent F: 40 mM HEPES buffer (pH 7.3)

EXAMPLE 12

Measurement of the samples 4, 5 and 6 were carried out in the same manner as in Example 6, with the exception that the eluent F was used having the following composition.

Eluent F: 40 mM BES buffer (pH 7.4)

EXAMPLE 13

Measurement of the samples 4, 5 and 6 were carried out in the same manner as in Example 6, with the exception that the eluent F was used having the following composition.

Eluent F: 20 mM maleate buffer (pH 6.8)

Measurement Results of Examples 7–13

As similar to Example 5, Examples 7–13 provided good results.

EXAMPLE 14

Semimicro System

Measurement was carried out in the same manner as in Example 6, except that the following measurement system and conditions were utilized.

System: delivery pump: Inert pump 2001, NANOSPACE SI-1 (manufactured by Shiseido Co., Ltd.)

autosampler: Autosampler 2003 (manufactured by Shiseido Co., Ltd.)

detector: UV-VIS detector 2002 (manufactured by Shiseido Co., Ltd.)

column: stainless steel column body (inner diameter 1.5 mm×40 mm long) packed with the packing material of Example 5 in the same fashion as in Example 5

Eluents: eluent E: 50 mM phosphate buffer containing 46 mM perchloric acid (pH 5.3)

eluent F: 25 mM tris(hydroxymethyl) amino-methane buffer (pH 7.5)

eluent H: 50 mM phosphate buffer containing 200 mM perchloric acid (pH 8.5)

During measurement, the eluent E was delivered for the initial 1.7-minute period, the eluent F for the next 1.8-minute period, the eluent H for the next 0.1-minute period and again the eluent E for the final 0.4-minute period.

Flow rate: 0.2 ml/min

Detection wavelength: 415 nm

Sample injection: 3 µl

Measurement Results

Figure 12:
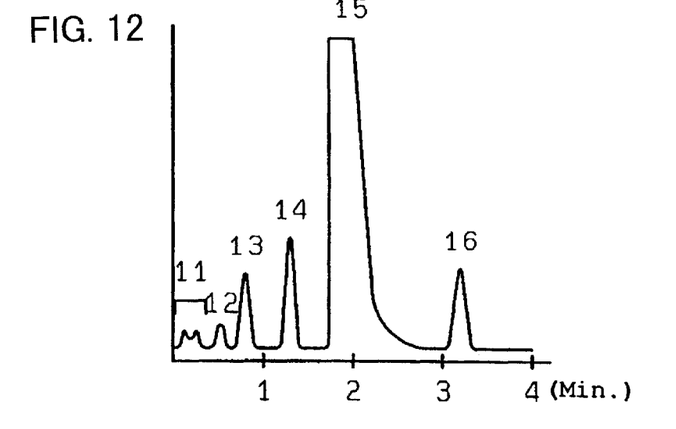
FIG. 12 shows a chromatogram obtained when separation of hemoglobin $A_2$ (sample 4) was carried out under the measurement conditions of Example 14.
Figure 13:
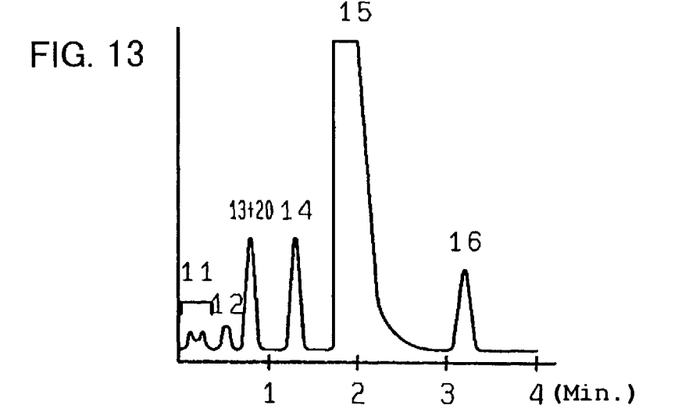
FIG. 13 shows a chromatogram obtained when separation of hemoglobin $A_2$ (sample 5) was carried out under the measurement conditions of Example 14.
Figure 14:
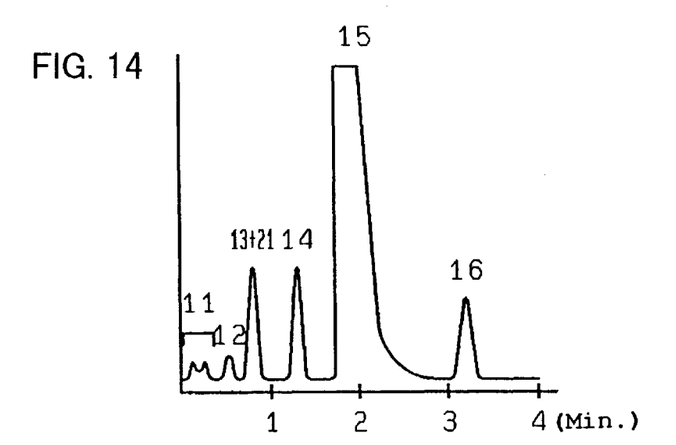
FIG. 14 shows a chromatogram obtained when separation of hemoglobin $A_2$ (sample 6) was carried out under the measurement conditions of Example 14.

The results obtained in Example 14 are shown in FIGS. 12–14. FIG. 12 show the measurement results obtained for the sample 4, FIG. 13 for the sample 5 and FIG. 14 for the sample 6. As analogous to the results of Example 5, stable $HbA_{1c}$ (Peak 14) was well separated from modified Hb such as CHb (Peak 20) or AHb (Peak 21). Also, $HbA_2$ (Peak 16) was separated in a satisfactory manner.

COMPARATIVE EXAMPLE 4

Measurement of the sample 4 was carried out in the same manner as in Example 6, except that the eluent F therein was replaced by the following eluent 2.

Eluent 2: 20 mM malate buffer (pH 5.7)

Measurement Results

Figure 15:
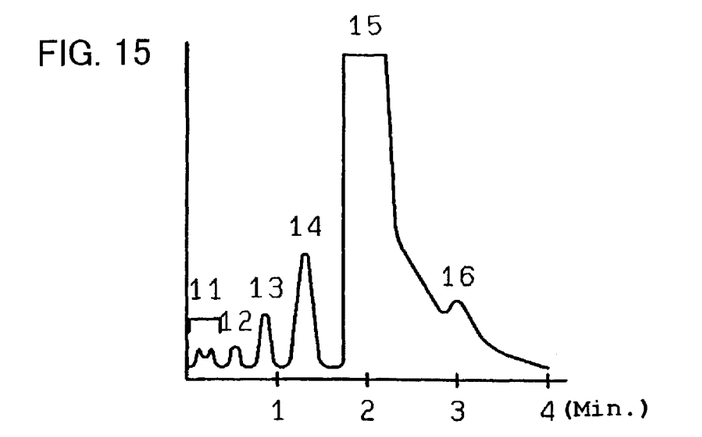
FIG. 15 shows a chromatogram obtained when separation of hemoglobin $A_2$ (sample 4) was carried out under the measurement conditions of Comparative Example 4.

As shown in FIG. 15, Comparative Example 4 resulted in the successful separation of stable $HbA_{1c}$ (Peak 14) but in the unsatisfactory separation of $HbA_2$ (Peak 16).

Evaluation of HbF, stable $HbA_{1c}$ and $HbA_2$ Measurement Precision

The measurement results obtained in Examples 5–10 and Comparative Example 4, each for the sample 4, are listed in Tables 3 and 4.

TABLE 3

| | Ex. 5 | | | Ex. 6 | | |
|---|---|---|---|---|---|---|
| | HbF | HbA1c | HbA2 | HbF | HbA1c | HbA2 |
| 1 | 0.5 | 5.1 | 2.3 | 0.5 | 5.2 | 2.3 |
| 2 | 0.5 | 5.1 | 2.3 | 0.5 | 5.1 | 2.3 |
| 3 | 0.5 | 5.2 | 2.3 | 0.5 | 5.2 | 2.3 |
| 4 | 0.5 | 5.1 | 2.3 | 0.5 | 5.1 | 2.3 |
| 5 | 0.5 | 5.2 | 2.3 | 0.5 | 5.2 | 2.3 |
| Mean | 0.50 | 5.14 | 2.30 | 0.50 | 5.16 | 2.30 |
| SD | 0.00 | 0.05 | 0.00 | 0.00 | 0.05 | 0.00 |
| CV % | 0.00 | 1.07 | 0.00 | 0.00 | 1.06 | 0.00 |
| | Ex. 7 | | | Ex. 8 | | |
| | HbF | HbA1c | HbA2 | HbF | HbA1c | HbA2 |
| 1 | 0.5 | 5.2 | 2.3 | 0.5 | 5.1 | 2.3 |
| 2 | 0.5 | 5.1 | 2.3 | 0.5 | 5.1 | 2.3 |
| 3 | 0.5 | 5.2 | 2.3 | 0.5 | 5.2 | 2.3 |
| 4 | 0.5 | 5.1 | 2.3 | 0.5 | 5.1 | 2.3 |
| 5 | 0.5 | 5.1 | 2.3 | 0.5 | 5.1 | 2.3 |
| Mean | 0.50 | 5.14 | 2.30 | 0.50 | 5.12 | 2.30 |
| SD | 0.00 | 0.05 | 0.00 | 0.00 | 0.04 | 0.00 |
| CV % | 0.00 | 1.07 | 0.00 | 0.00 | 0.87 | 0.00 |

TABLE 4

| | Ex. 9 | | | Ex. 10 | | |
|---|---|---|---|---|---|---|
| | HbF | HbA1c | HbA2 | HbF | HbA1c | HbA2 |
| 1 | 0.5 | 5.1 | 2.3 | 0.5 | 5.2 | 2.3 |
| 2 | 0.5 | 5.1 | 2.3 | 0.5 | 5.2 | 2.3 |
| 3 | 0.5 | 5.1 | 2.3 | 0.5 | 5.2 | 2.3 |
| 4 | 0.5 | 5.1 | 2.3 | 0.5 | 5.1 | 2.3 |
| 5 | 0.5 | 5.1 | 2.3 | 0.5 | 5.1 | 2.3 |
| Mean | 0.50 | 5.10 | 2.30 | 0.50 | 5.16 | 2.30 |
| SD | 0.00 | 0.00 | 0.00 | 0.00 | 0.05 | 0.00 |
| CV % | 0.00 | 0.00 | 0.00 | 0.00 | 1.06 | 0.00 |
| | Comp. Ex. 4 | | | | | |
| | HbF | HbA1c | HbA2 | | | |
| 1 | 0.5 | 5.1 | 0.9 | | | |
| 2 | 0.5 | 5.1 | 3.1 | | | |
| 3 | 0.5 | 5.2 | 3.5 | | | |
| 4 | 0.5 | 5.1 | 2.4 | | | |
| 5 | 0.5 | 5.1 | 2.3 | | | |
| Mean | 0.50 | 5.12 | 2.44 | | | |
| SD | 0.00 | 0.04 | 0.99 | | | |
| CV % | 0.00 | 0.87 | 40.74 | | | |

As can be seen from the measurement results of Examples 5–10, the measurement precision (CV values) was very high for HbA$_2$ and satisfactory for HbF and stable HbA$_{1\,c}$. Also, all the Examples gave the HbA$_2$ level of 2.3 %, demonstrating the superior measurement precision for HbA$_2$. On the other hand, the measurement precision was very low in Comparative Example 4.

EXAMPLE 15

For the below-specified measurement samples 7 and 8, separation of hemoglobin A$_2$ was carried out under the same conditions as in Example 5, except that the eluents were used having the following compositions.

Eluents: eluent E: 25 mM succinate-20 mM phosphate buffer containing 50 mM perchloric acid and 0.03 wt. % sodium azide (pH 5.3)

eluent F: 10 mM phosphate buffer containing 0.03 wt. % sodium azide (pH 7.1)

eluent G: 5 mM succinate-15 mM phosphate buffer containing 90 mM perchloric acid containing 0.03 wt. % sodium azide (pH 5.3)

eluent H: 20 mM succinate-20 mM phosphate buffer containing 250 mM perchloric acid (pH 8.4)

During measurement, the eluent E was delivered for the initial 1.7-minute period, the eluent F for the next 1.3-minute period, the eluent G for the next 0.5-minute period, the eluent H for the next 0.1-minute period and again the eluent E for the final 0.4-minute period.

Flow rate: 2.0 ml/min

Detection wavelength: 415 nm

Sample injection: 10 µl

Measurement Sample 7

In accordance with the appended documents, Hemoglobin A$_2$ Control Level 2 (product of Bio-Laboratories Inc.) was allowed to dissolve in 1 ml water and then hemolytically diluted with a 60-fold amount of a hemolyzing solution (phosphate buffer (pH 7) containing, as a surfactant, 0.1 wt. % polyethylene glycol mono-4-octylphenyl ether (Triton X-100, manufactured by Tokyo Kasei Co., Ltd.)) to prepare a measurement sample 7.

Measurement Sample 8

Hemoglobin AFSC HEMO Control (product of Helena Laboratories Inc.) was hemolytically diluted with a 60-fold amount of a hemolyzing solution (phosphate buffer (pH 7) containing, as a surfactant, 0.1 wt. % polyethylene glycol mono-4-octylphenyl ether (Triton X-100, manufactured by Tokyo Kasei Co., Ltd.)) to prepare a measurement sample 8.

Measurement Results

Figure 16:
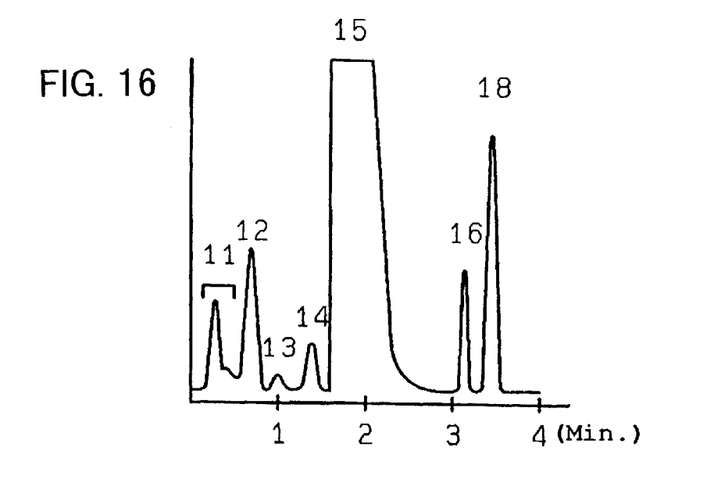
FIG. 16 shows a chromatogram obtained when separation of hemoglobin $A_2$ (sample 7) was carried out under the measurement conditions of Example 15.
Figure 17:
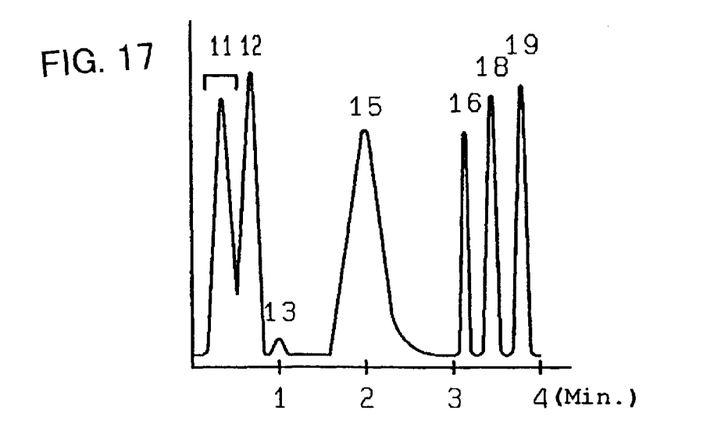
FIG. 17 shows a chromatogram obtained when separation of hemoglobin $A_2$ (sample 8) was carried out under the measurement conditions of Example 15.

The chromatograms obtained in Example 15 are shown in FIGS. 16 and 17. FIG. 16 shows the results obtained for the sample 7 and FIG. 17 for the sample 8. As apparent from FIGS. 16 and 17 the separation of HbF, stable HbA$_1$, HbA$_2$, HbS and HbC was achieved in a satisfactory fashion. As shown in Table 5, the measurement precision was also satisfactory.

TABLE 5

| | Sample 7 | | | | Sample 8 | | | |
|---|---|---|---|---|---|---|---|---|
| | HbF | HbA1c | HbA2 | HbS | HbF | HbA2 | HbS | HbC |
| 1 | 8.3 | 2.1 | 5.4 | 27.1 | 24.1 | 3.1 | 18.7 | 17.7 |
| 2 | 8.3 | 2.1 | 5.4 | 27.2 | 24.2 | 3.1 | 18.7 | 17.8 |
| 3 | 8.2 | 2.1 | 5.5 | 27.2 | 24.1 | 3.1 | 18.8 | 17.7 |
| 4 | 8.3 | 2.1 | 5.5 | 27.1 | 24.1 | 3.1 | 18.7 | 17.7 |
| 5 | 8.3 | 2.1 | 5.4 | 27.2 | 24.2 | 3.2 | 18.8 | 17.7 |
| Mean | 8.28 | 2.10 | 5.44 | 27.16 | 24.14 | 3.12 | 18.74 | 17.72 |
| SD | 0.04 | 0.00 | 0.05 | 0.05 | 0.05 | 0.04 | 0.05 | 0.04 |
| CV % | 0.54 | 0.00 | 1.01 | 0.20 | 0.23 | 1.43 | 0.29 | 0.25 |

EXAMPLE 16

Measurement of hemoglobins was carried out under the same conditions as in Example 15, except that the eluent E was used having the following composition.

Eluent E: 25 mM succinate-20 mM phosphate buffer containing 50 mM perchloric acid (pH 5.3)

Measurement Results

Figure 18:
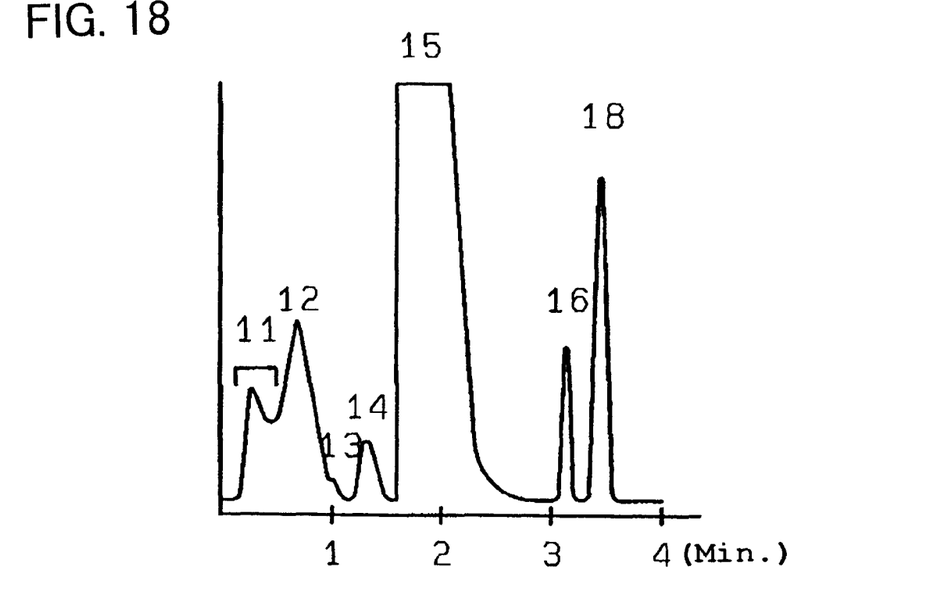
FIG. 18 shows a chromatogram obtained when separation of hemoglobin $A_2$ (sample 7) was carried out under the measurement conditions of Example 16.
Figure 19:
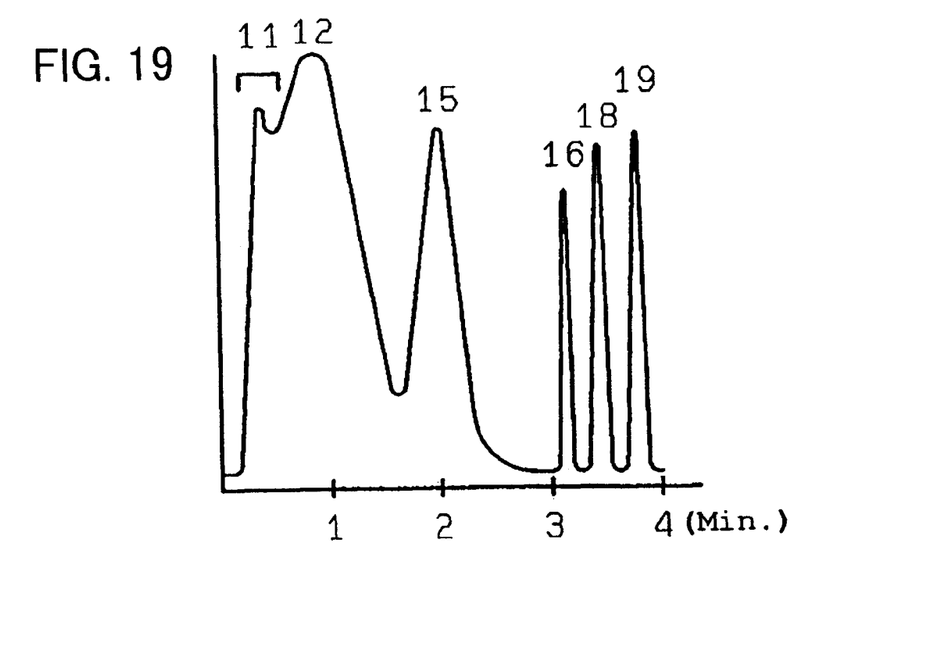
FIG. 19 shows a chromatogram obtained when separation of hemoglobin $A_2$ (sample 8) was carried out under the measurement conditions of Example 16.

The chromatograms obtained in Example 16 are shown in FIGS. 18 and 19. FIG. 18 shows the results obtained for the sample 7 and FIG. 19 for the sample 8. As can be seen from FIGS. 18 and 19, Example 16 resulted in satisfactory separation of $HbA_2$, HbS and HbC but in poor separation of HbF.

EFFECTS OF THE INVENTION

Because of the constitution as described above, the practice of the present invention results in the more precise and quicker separation of $HbA_2$ from a Hb mixture relative to conventional methods.

What is claimed is:

1. A method for separating hemoglobin $A_2$ from a hemoglobin mixture according to a cation exchange liquid chromatographic technique, characterized that at least two types of eluents are used including an eluent (hereinafter referred to as "eluent A") for elution of faster hemoglobins than hemoglobin $A_0$ and an eluent (hereinafter referred to as "eluent B") for elution of hemoglobin $A_0$ and slower hemoglobins than hemoglobin $A_0$ and that said eluent A has a pH of 4.0–6.0 and said eluent B is maintained at a pH of at least 0.5 higher than that of the eluent A.

2. The method for separating hemoglobin $A_2$ as recited in claim 1, characterized that said eluent B is lower in salt concentration than said eluent A.

3. The method for separating hemoglobin $A_2$ as recited in claim 1, wherein an eluent (hereinafter referred to as "eluent D") is further used for elution of at least hemoglobin $A_2$ and that said eluent D is maintained at a pH of at least 0.5 lower than that of said eluent B.

4. The method for separating hemoglobim $A_2$ as recited in claim 3, characterized that said eluent B is lower in salt concentration than said eluent A and said lower in salt concentration than said eluent A and said eluent D is higher in salt concentration than the eluent B.

5. method for separating hemoglobin $A_2$ as recited in claim 3, wherein an eluent (herinafter referred to as "eluent C") is further used having a weaker elution power than said eluents B and D, and that said eluents are delivered in the sequence of B,C and D.

6. The method for separating hemoglobin $A_2$ as recited in claim 1, wherein an eluent H at a pH of 6.8–12 is delivered to follow said eluent B or D.

7. The method for separating hemoglobin $A_2$ as recited in claim 6, characterized that said eluent H contains a chaotropic ion.

8. The method for separating hemoglobin $A_2$ as recited in claim 1, wherein at least one of said eluents and/or a hemolyzing solution contains an azide ion.

9. The method for separating hemoglobin $A_2$ as recited in claim 1, wherein a packing material is used having at least one type of strong cation exchange group.

10. A method for separating hemoglobin $A_2$ from a hemoglobin mixture according to a cation exchange liquid chromatographic technique, characterized that at least two types of eluents are used including an eluent (hereinafter referred to as "eluent E") which contains a chaotropic ion and also contains an inorganic acid, organic acid and/or any salt thereof having a buffer capacity at a pH of 4.0–6.8 and an eluent (hereinafter referred to as "eluent F") which contains an inorganic acid, organic acid and/or any salt thereof having a buffer capacity at a pH of 6.5–8.0.

11. The method for separating hemoglobin $A_2$ as recited in claim 10, characterized that an eluent (hereinafter referred to as "eluent G") is further used having a lower pH and a higher salt concentration relative to said eluent F, and that said eluent G is delivered to follow the eluent F.

12. The method for separating hemoglobin $A_2$ as recited in claim 10, wherein an eluent H at a pH of 6.8–12 is delivered to follow said eluent F or G.

13. The method for separating hemoglobin $A_2$ as recited in claim 12, characterized that said eluent H contains a chaotropic ion.

* * * * *